(12) United States Patent
McFerrin

(10) Patent No.: US 9,867,405 B1
(45) Date of Patent: Jan. 16, 2018

(54) HEAD COOLING APPARATUS

(71) Applicant: Stuart McFerrin, Knoxville, TN (US)

(72) Inventor: Stuart McFerrin, Knoxville, TN (US)

( * ) Notice: Subject to any disclaimer, the term of this patent is extended or adjusted under 35 U.S.C. 154(b) by 331 days.

(21) Appl. No.: 14/464,207

(22) Filed: Aug. 20, 2014

Related U.S. Application Data

(60) Provisional application No. 61/874,421, filed on Sep. 6, 2013.

(51) Int. Cl.
*A41D 13/005* (2006.01)

(52) U.S. Cl.
CPC ...... *A41D 13/0053* (2013.01); *A41D 2600/20* (2013.01)

(58) Field of Classification Search
CPC .......... A41D 13/0053; A41D 2400/422; A41D 2600/20; A61F 7/10; A61F 2007/0233; A62B 17/005; F25D 2400/26; F25D 3/08; F25D 17/06; F25D 2303/083; F25D 2303/084; F25D 2331/801; F25D 2600/02; F25D 2700/12
See application file for complete search history.

(56) References Cited

U.S. PATENT DOCUMENTS

| | | | |
|---|---|---|---|
| 3,406,678 A | 10/1968 | Hanks | |
| 4,459,822 A | 7/1984 | Pasternack | |
| 4,546,820 A * | 10/1985 | Whipple | B23P 15/26 165/77 |
| 4,566,455 A | 1/1986 | Kramer | |
| 4,691,762 A * | 9/1987 | Elkins | A61F 7/02 165/46 |
| 4,781,193 A * | 11/1988 | Pagden | A61F 7/007 607/104 |
| 4,998,415 A * | 3/1991 | Larsen | A41D 13/0053 62/231 |
| 5,940,880 A | 8/1999 | Phillips | |
| 6,030,412 A * | 2/2000 | Klatz | A61F 7/00 607/104 |

(Continued)

FOREIGN PATENT DOCUMENTS

| | | | |
|---|---|---|---|
| CA | 2432852 A1 * | 12/2004 | ......... A41D 13/0053 |
| EP | 1080648 | 3/2001 | |

(Continued)

*Primary Examiner* — Emmanuel Duke
(74) *Attorney, Agent, or Firm* — Matthew M. Googe; Robinson IP Law, PLLC

(57) ABSTRACT

A head cooling apparatus is provided for cooling a head of a user. The head cooling apparatus includes a portable pump assembly having a foldable heat exchanger formed into a pocket to substantially receive a replaceable cooling source, the foldable heat exchanger including a first exchanger half including a channel, a center portion connected to the first exchanger half, and a second exchanger half connected to the center portion. The head cooling apparatus also includes a headgear assembly in fluid communication with the portable pump assembly, the headgear assembly configured to be worn adjacent a user's head, the headgear assembly including a conformable pouch configured to be positioned adjacent a user's head. The first exchanger half and second exchanger half are foldable along the center portion such that a replaceable cooling source is substantially sandwiched between the first exchanger half and second exchanger half.

17 Claims, 11 Drawing Sheets

(56) References Cited

U.S. PATENT DOCUMENTS

| | | | |
|---|---|---|---|
| 7,296,304 B2 | 11/2007 | Goldsborough | |
| 7,921,473 B1 | 4/2011 | Winters | |
| 8,297,070 B2 | 10/2012 | Pryor | |
| 2002/0153126 A1* | 10/2002 | Clemente | A41D 13/005 165/46 |
| 2003/0176902 A1 | 9/2003 | Gunn et al. | |
| 2004/0074250 A1 | 4/2004 | Junkins | |
| 2004/0206485 A1* | 10/2004 | Ferraro | F24B 9/006 165/156 |
| 2006/0191063 A1 | 8/2006 | Elkins et al. | |
| 2010/0032132 A1 | 2/2010 | Collins | |
| 2010/0106229 A1* | 4/2010 | Gammons | A61F 7/0085 607/104 |
| 2012/0151951 A1* | 6/2012 | Terry | A61F 7/02 62/259.3 |

FOREIGN PATENT DOCUMENTS

| | | | | |
|---|---|---|---|---|
| JP | 09042697 A | * | 2/1997 | |
| JP | H0942697 A | * | 2/1997 | F24F 1/00 |

* cited by examiner

HEAD COOLING APPARATUS

CROSS-REFERENCE(S) TO RELATED APPLICATION(S)

This application claims priority to U.S. Application Ser. No. 61/874,421 to Stuart McFerrin for a "Head Cooling Apparatus" which was filed on Sep. 6, 2013, the content of which is incorporated herein by reference in its entirety.

FIELD

This disclosure relates to the field of personal cooling devices. More particularly, this disclosure relates to a personal cooling apparatus for cooling the head of a user.

BACKGROUND

In many occupations a person may be exposed to environments of elevated temperatures. Further, the environment in which the elevated temperatures are present may be relatively confined and therefore require that a person accessing the elevated temperature environment position themselves in various orientations while in the particular environment.

For example, when a person has to access an attic or rooftop to perform repairs or otherwise perform work within the attic or on the rooftop, the person may be required to crawl or lie down while accessing the attic or rooftop. Temperatures in attics may become extremely high while the person is in the attic or rooftop. Other environments of elevated temperatures may include sporting events or other outdoor activities.

What is needed, therefore, is a personal cooling apparatus for cooling the head of a user while the user is in various positions in an environment of elevated temperatures.

SUMMARY

The above and other needs are met by a head cooling apparatus for cooling the head of a user while the user is in various positions in an environment of elevated temperatures. The head cooling apparatus includes a portable pump assembly, a headgear assembly configured to be worn adjacent a user's head, the headgear assembly comprising a second heat exchanger positioned adjacent a user's head, a headgear assembly inlet port and a headgear assembly outlet port, a first flexible fluid transfer conduit secured to the outlet port of the portable pump assembly and the headgear assembly inlet port, and a second flexible fluid transfer conduit secured to the inlet port of the pump assembly and the headgear assembly outlet port. The portable pump assembly includes a replaceable cooling source, a first heat exchanger adjacent the replaceable cooling source, a pump in fluid communication with the first heat exchanger, an inlet port, and an outlet port. The portable pump assembly, headgear assembly, first flexible fluid transfer conduit and second fluid transfer conduit form a loop that is substantially sealed such that no air is present in the loop so that the portable pump assembly circulates a fluid within the loop regardless of an orientation of a user.

In one embodiment, the second heat exchanger of the headgear assembly is formed of a conformable pouch including a plurality of lobes, wherein a path is formed through the conformable pouch such that a fluid flows into the conformable pouch through the headgear assembly inlet port, through each of the lobes, and out of the headgear assembly outlet port. In another embodiment, the conformable pouch includes four lobes. In yet another embodiment, the conformable pouch further includes a plurality of dimples formed therein.

In one embodiment, the headgear assembly further includes a head cover. In another embodiment, the plurality of lobes are adjustable such that one or more of the lobes may be sized to fit within various head covers.

In yet another embodiment, the first heat exchanger is a foldable exchanger that forms a pocket to substantially receive the replaceable cooling source.

In one embodiment, the foldable exchanger includes a first exchanger half including a channel, an inlet port, and an outlet port, a center portion connected to the first exchanger half, and a second exchanger half connected to the center portion, the second exchanger half including a channel, an inlet port, and an outlet port. The first exchanger half and second exchanger half are foldable along the center portion such that a replaceable cooling source is substantially sandwiched between the first exchanger half and second exchanger half.

In another embodiment, the head cooling apparatus further includes a thermostat in electrical communication with the pump for detecting a temperature of a fluid in either of the headgear assembly or portable pump assembly. In yet another embodiment, the head cooling apparatus further includes a timer in electrical communication with the pump for activating and deactivating the inline pump for a desired period of time.

In another aspect, embodiments of the disclosure provide a head cooling apparatus including a portable pump assembly and a headgear assembly in fluid communication with the portable pump assembly, the headgear assembly configured to be worn adjacent a user's head, the headgear assembly including a conformable pouch configured to be positioned adjacent a user's head, the conformable pouch including an inlet port and an outlet port. The portable pump assembly includes a foldable heat exchanger formed into a pocket to substantially receive a replaceable cooling source and a pump in fluid communication with the foldable heat exchanger.

In one embodiment, the headgear assembly further includes a head cover. In another embodiment, the headgear assembly includes a plurality of lobes wherein a path is formed through the conformable pouch such that a fluid flows into the conformable pouch through the headgear assembly inlet port, through each of the lobes, and out of the headgear assembly outlet port. In yet another embodiment, the conformable pouch includes four lobes.

In one embodiment, the conformable pouch further includes a plurality of dimples formed therein. In another embodiment, the plurality of lobes are adjustable such that one or more of the lobes may be sized to fit within various head covers.

In yet another embodiment, the foldable head exchanger includes a first exchanger half including a channel, an inlet port, and an outlet port, a center portion connected to the first exchanger half, a second exchanger half connected to the center portion, the second exchanger half including a channel, an inlet port, and an outlet port. The first exchanger half and second exchanger half are foldable along the center portion such that a replaceable cooling source is substantially sandwiched between the first exchanger half and second exchanger half.

In one embodiment, the head cooling apparatus includes a thermostat in electrical communication with the pump for detecting a temperature of a fluid in either of the headgear assembly or portable pump assembly. In another embodiment, the head cooling apparatus includes a timer in electrical communication with the pump for activating and deactivating the inline pump for a desired period of time.

In yet another aspect, embodiments of the disclosure provide a head cooling apparatus including a portable pump assembly and a headgear assembly in fluid communication with the portable pump assembly, the headgear assembly configured to be worn adjacent a user's head, the headgear assembly including a conformable pouch configured to be positioned adjacent a user's head, the conformable pouch including an inlet port and an outlet port. The portable pump assembly includes a foldable heat exchanger formed into a pocket to substantially receive a replaceable cooling source. The foldable heat exchanger includes a first exchanger half including a channel, an inlet port, and an outlet port, a center portion connected to the first exchanger half, and a second exchanger half connected to the center portion, the second exchanger half including a channel, an inlet port, and an outlet port. The first exchanger half and second exchanger half are foldable along the center portion such that a replaceable cooling source is substantially sandwiched between the first exchanger half and second exchanger half.

In related embodiments, a head heat transfer apparatus including the various features described above is disclosed. In certain embodiments, the head heat transfer apparatus is configured to heat the head of a user.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

Figure 1:
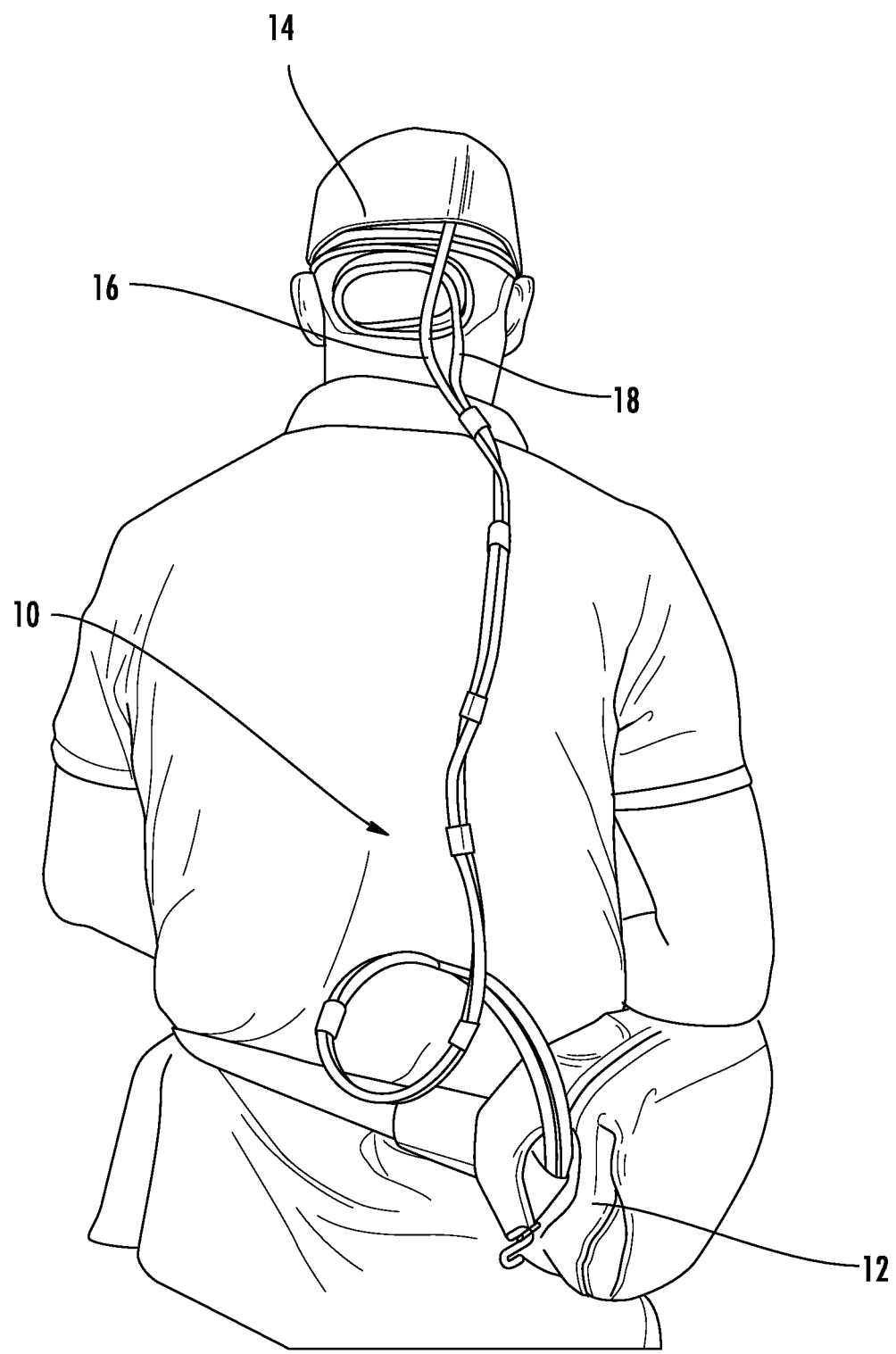
FIG. 1 shows a perspective view of a head cooling apparatus according to one embodiment of the disclosure.

FIG. 1 shows a basic embodiment of a head cooling apparatus 10 of the present disclosure as worn by a user. The head cooling apparatus includes a portable pump assembly 12 and a headgear assembly 14, the headgear assembly 14 being positioned adjacent a head and neck of a user. The pump assembly 12 and headgear assembly 14 are in fluid communication with each other through flexible fluid transfer conduits 16 and 18.

Figure 2:
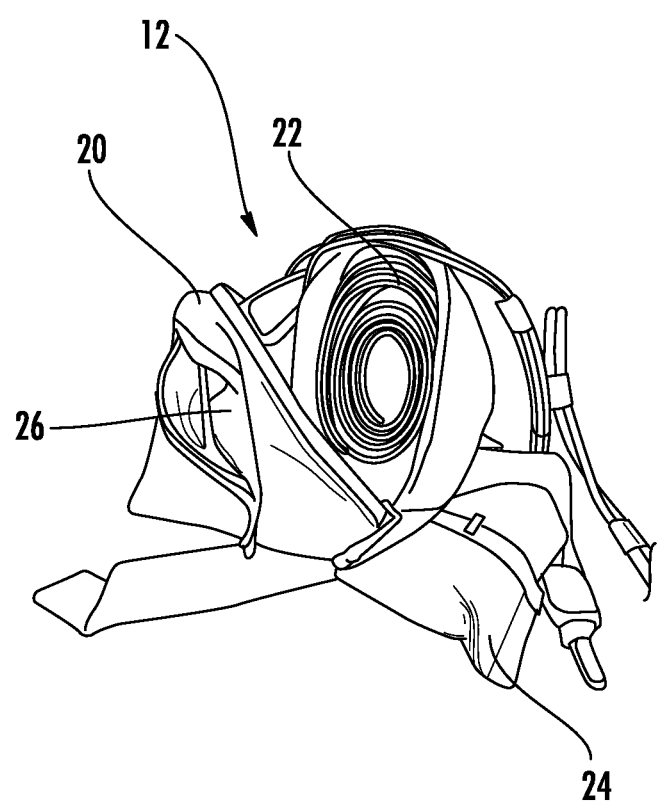
FIG. 2 shows a perspective view of a portable pump assembly of a head cooling apparatus according to one embodiment of the disclosure.

Referring now to FIG. 2, the portable pump assembly 12 includes a housing 20, a first heat exchanger 22, a replaceable cooling source 24, and a pump 26. The first heat exchanger 22, replaceable cooling source 24, and pump 26 are preferably located within the housing 20. The housing 20 may comprise a pack as shown in FIG. 2, such as a belt pack or a backpack, thereby making the portable pump assembly 12 easily wearable by the user.

The first heat exchanger 22 may be formed in a coil or other like shape to substantially increase a surface area of the first heat exchanger 22. The first heat exchanger 22 is formed of a material having high thermal conductivity, such as aluminum or other like metals. However, it is also understood that the first heat exchanger 22 may also be formed of a flexible material such as polyurethane, polyethylene, PVC or other similar materials.

The housing 20 forms a cavity for accepting the replaceable cooling source 24 and maintaining the replaceable cooling source 24 adjacent the coiled first heat exchanger 22. The replaceable cooling source 24 may be formed of a sac or block filled with ice (including, for example, solid water and/or solid carbon dioxide), refrigerant gel or liquid, or other cooled materials. The replaceable cooling source 24 may be stored in a cool environment such as a freezer or refrigerator and placed within the housing 20 adjacent the first heat exchanger 22 when the user desires to wear the head cooling apparatus 10.

The pump 26 is in fluid communication with the first heat exchanger 22 for pumping a fluid from the portable pump assembly 12 to the headgear assembly 14. As referred to herein, a pump is configured to receive a fluid at an inlet pressure and discharge the fluid at a higher outlet pressure. The inline pump moves fluid through the head cooling apparatus 10 without requiring a fluid reservoir, such as with an inline pump and may be an electromechanical pump or a manual pump operated by a user. The pump 26 may be powered by a power source such as a battery and includes a power switch for activating and deactivating the pump 26. While FIGS. 1 and 2 show the pump 26 located within the portable pump assembly 12, it is also understood that the pump 26 may be positioned adjacent the headgear assembly 14 or between the headgear assembly and portable pump assembly 12.

The portable pump assembly 12 includes an outlet port for discharging cooled fluid from the portable pump assembly 12 and an inlet port for receiving fluid returning to the portable pump assembly from the headgear assembly 14.

Figure 9:
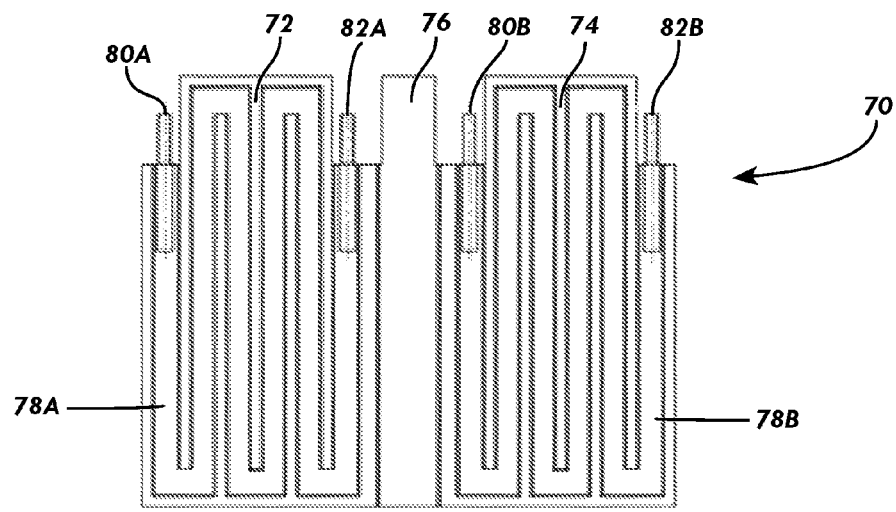
Figure 10:
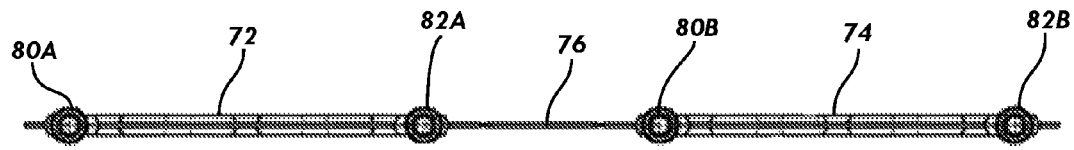

FIGS. 6-12 illustrate one preferably embodiment of the portable pump assembly 12 wherein the first heat exchanger 22 is formed of a foldable exchanger 70 formed of a first exchanger half 72, a second exchanger half 74, and a center portion 76 connecting the first exchanger half 72 to the second exchanger half 74 (FIGS. 9 and 10). Each of the first exchanger half 72 and second exchanger half 74 includes a channel 78A and 78B in fluid communication with inlet ports 80A and 80B and outlet ports 82A and 82B.

The foldable exchanger 70 is folded along the center portion 76 such that the first exchanger half 72 and second exchanger half 74 preferably extend substantially parallel to each other from the center portion 76 and such that the first exchanger half 72 and second exchanger half 74 are spaced apart from each other to create a pocket. The pocket is sized to receive the replaceable cooling source 24 such that the channel 78A and 78B contact both a first side and a second side of the cooling source 24 to maximize surface area adjacent the cooling source 24, thereby substantially sandwiching the replaceable cooling source 24 between the first exchanger half 72 and the second exchanger half 74. A fluid may enter the first exchanger half inlet port 80A and exit the first exchanger outlet port 82A. The first exchanger outlet port 82A may be in communication with the second exchanger half inlet port 80B such that a fluid flows through the second exchanger half 74 and out of the second exchanger half outlet port 82B. As a fluid passes through the channel 78A and 78B, the fluid is substantially cooled by the cooling source 24 before exiting the foldable exchanger 70.

Figure 11:
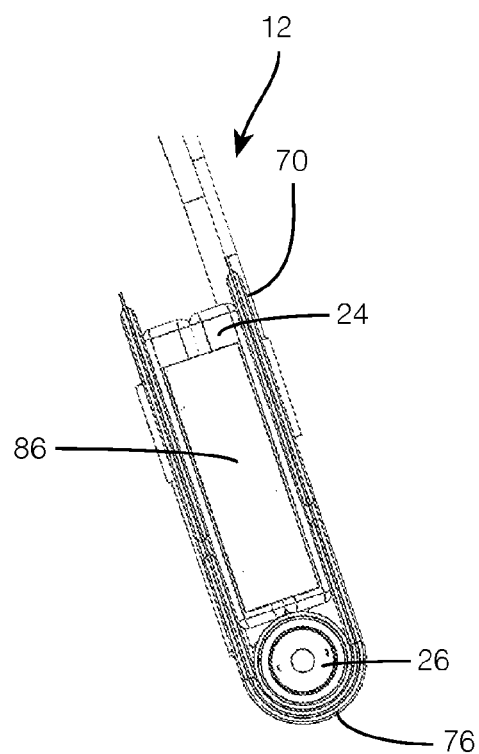
FIGS. 11 and 12 show a portable pump assembly of a head cooling apparatus according to one embodiment of the disclosure.
Figure 12:
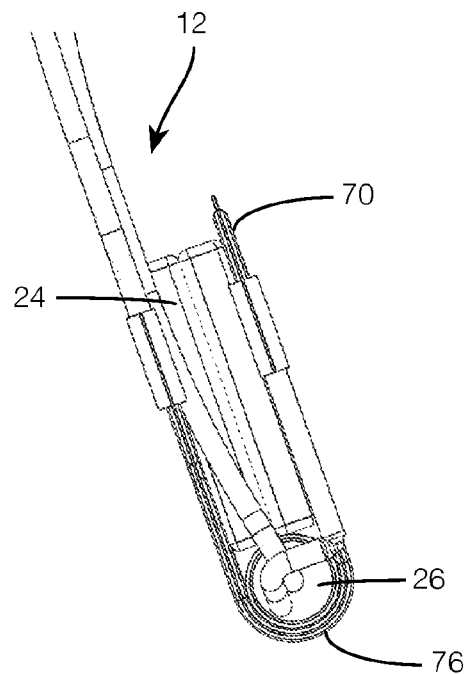

The foldable exchanger 70 may further be configured to receive the pump 26 adjacent the center portion 76, as illustrated in FIGS. 11 and 12. The center portion 76 of the foldable exchanger 70 may substantially wrap around the pump 26 such that the pump 26 is contained within the foldable exchanger 70, thereby maintaining the foldable exchanger 70 and pump 26 as a single piece. A battery 86 may further be connected adjacent a cooling source and within the foldable exchanger 70 such that the battery 86 is also part of a single piece including the foldable exchanger 70 and pump 26.

The pump assembly 12 including the foldable exchanger 70 illustrated in FIGS. 11 and 12 may be oriented to fit within a housing 20, such as a bag or pack. The foldable exchanger 70 is oriented such that a replaceable cooling source may be inserted from a top of the foldable exchanger 70 and such that the first exchanger half inlet port 80A is at a bottom of the foldable exchanger to receive a fluid from the pump 26. While the above contemplates receiving a replaceable cooling source from a top of the foldable exchanger 70 and positioning a pump adjacent a bottom of the foldable exchanger 70, it is also understood that the foldable exchanger may be oriented such that the foldable exchanger receives a replaceable cooling source from a bottom of the foldable exchanger 70 and that a pump may be adjacent a top of the foldable exchanger 70.

Figure 3:
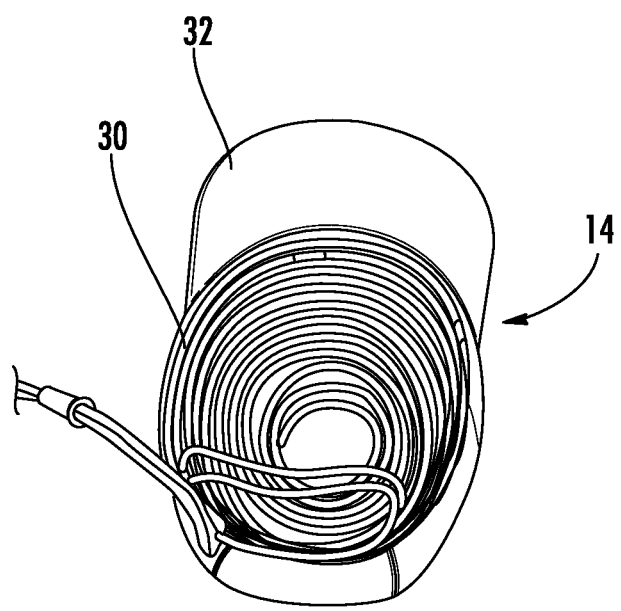
FIG. 3 shows a close-up view of a headgear assembly of a head cooling apparatus according to one embodiment of the disclosure.
Figure 4:
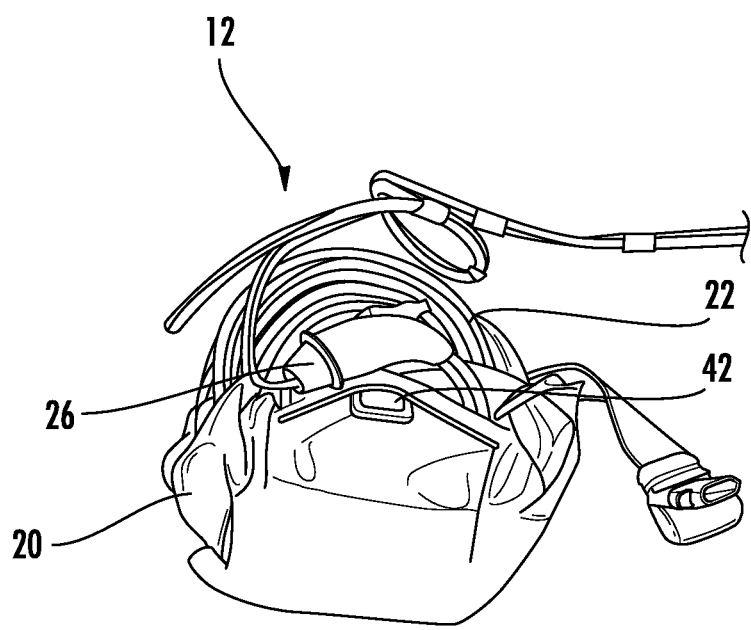
FIG. 4 shows a side view of a portable pump assembly of a head cooling apparatus according to one embodiment of the disclosure.

Referring now to FIG. 3, the headgear assembly 14 includes a second heat exchanger 30 and a head cover 32. The second heat exchanger 30 may be formed in a coil or other shape that is conformed to fit adjacent the head and neck of the user to substantially increase contact surface area between the second heat exchanger 30 and the skin of the user. The second exchanger 30 may be formed of a material having high thermal conductivity, such as aluminum or other like metals. However, it is also understood that the second heat exchanger may also be formed of a flexible material such as polyurethane, polyethylene, PVC or other similar flexible materials for conforming to a shape of the user's head.

For example, in one embodiment the second heat exchanger 30 is a flexible tubing formed from materials such as polyurethane, polyethylene, PVC or other like materials and is sewn into seams of a head cover 32 such as a baseball hat. The head cover 32 may be elastic such that the flexible second heat exchanger 30 stretches with the flexible head cover 32, thereby making the headgear assembly 14 adaptable to a variety of user head sizes. The flexible second heat exchanger 30 also has a low profile such that the headgear assembly 14 is minimally intrusive to the user and therefore allows protective headwear to be worn over the headgear assembly 14 such as hard hats and helmets.

The head cover 32 may be formed of a hat or other headwear and is configured to fit over the second heat exchanger 30 to insulate the second heat exchanger 30 and otherwise conceal the appearance of the second exchanger 30.

The headgear assembly 14 includes a headgear assembly inlet port and a headgear assembly outlet port in fluid communication with the second heat exchanger 30.

Figure 13:
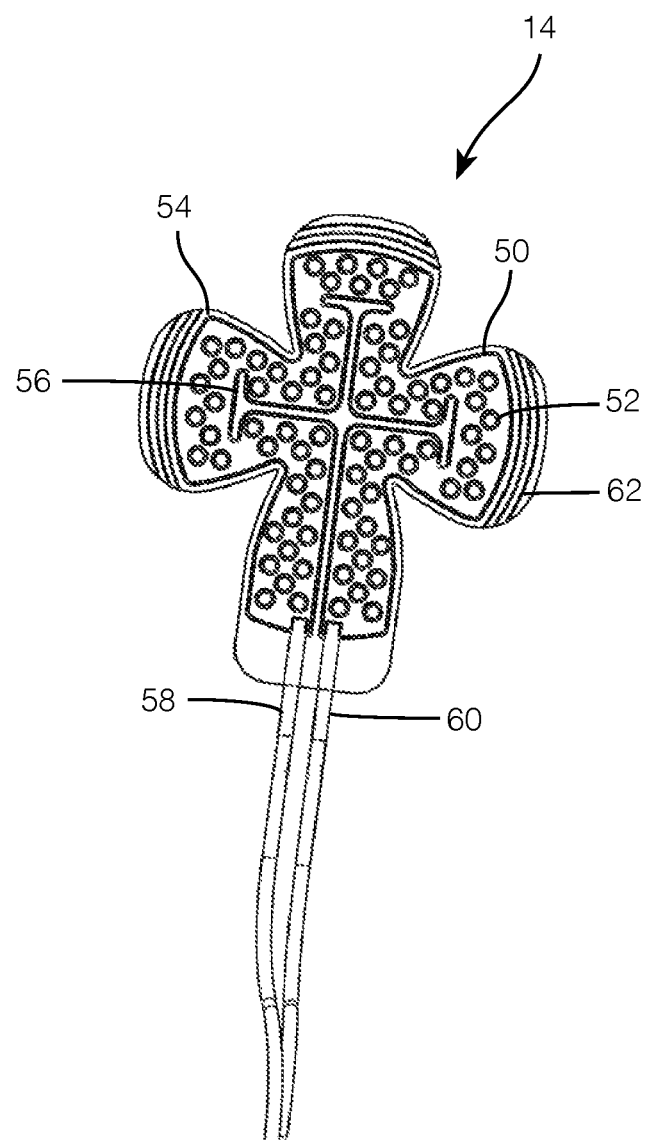
FIG. 13 shows a headgear assembly of a head cooling apparatus according to one embodiment of the disclosure.

Referring now to FIG. 13, in a preferable embodiment the second exchanger 30 of the headgear assembly 14 is formed of a conformable pouch 50. The conformable pouch 50 is preferably substantially clover-shaped such that the pouch 50 is formed of a plurality of interconnected lobes 54, preferably four, and includes a plurality of dimples 52 formed in the lobes 54. A cross-shaped indentation 56 is formed in a center of the pouch 50 and separates each of the lobes 54 such that a path is created for fluid to flow into the pouch 50 from an inlet port 58, through each of the lobes 54, and then out of an outlet port 60. An end of each of the lobes 54 includes one or more guidelines 62 that allow the lobes 54 to be trimmed such that the conformable pouch 50 may be sized to fit within various head covers 32. The conformable pouch 50 has a substantially thin profile for fitting within the head cover 32 and conforming to the user's head.

The conformable pouch 50 may include the plurality of dimples 52 formed therein. The dimples are formed in a surface of the pouch 50 that is adjacent to a user's head and extend into the pouch 50 such that the dimples 52 contact and connect to a surface of the pouch 50 that is distal from a user's head. The dimples 52, connected to a distal surface of the pouch 50, maintain the pouch in a substantially minimal profile such that when a fluid flows through the pouch 50 a thickness of the pouch 50 is maintained at a desired thickness without the pouch 50 over-expanding. The plurality of dimples 52 further increase a cooling area adjacent a user's head and create a plurality of air pockets for further cooling a user's head.

While it is understood that the pouch 50 described above is preferably clover-shaped, it is also understood that the pouch 50 may be formed of various other shapes suitable for contacting a head of a user to substantially cool a head of a user. For example, the pouch 50 may be substantially X-shaped, cross-shaped, circular, or other various shapes.

Referring again to FIG. 1, a pair of flexible fluid transfer conduits 16 and 18 are positioned between the portable pump assembly 12 and the headgear assembly 14 and are in fluid communication with the headgear assembly and portable pump assembly inlet and outlet ports for transferring fluid between the portable pump assembly 12 and headgear assembly 14. The flexible fluid transfer conduits 16 and 18 are preferably formed of flexible tubing such as polyurethane, polyethylene, PVC or other like flexible tubing materials.

Figure 5:
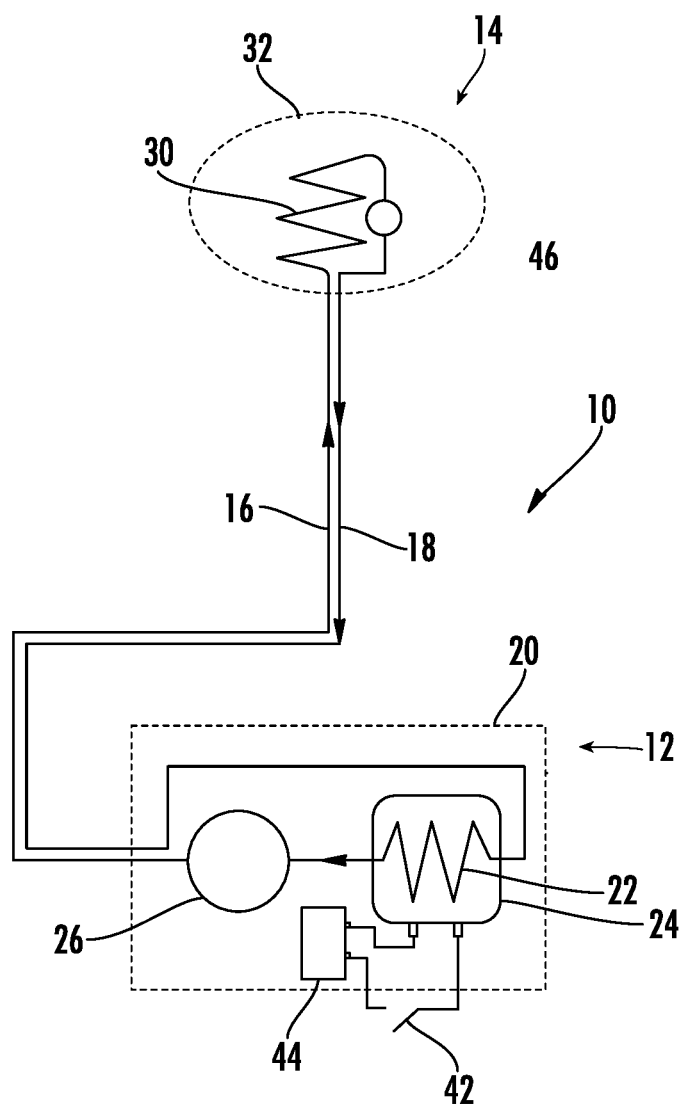
FIG. 5 shows a schematic diagram of a head cooling apparatus according to one embodiment of the disclosure.
Figure 6:
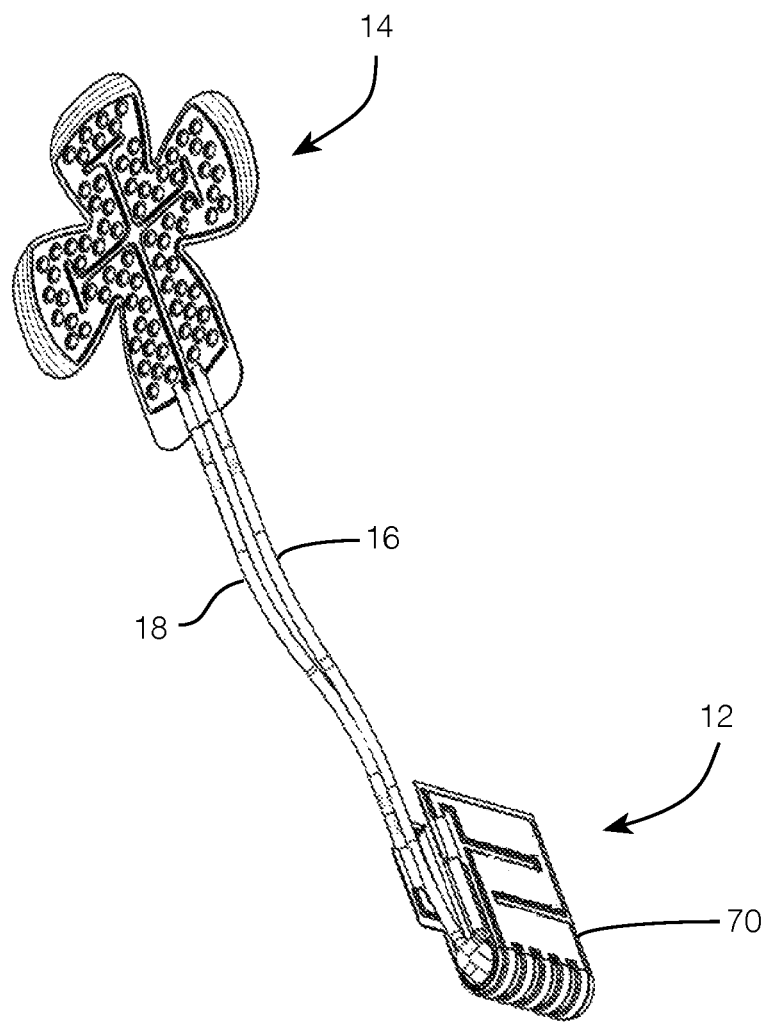
FIG. 6 shows a perspective view of a head cooling apparatus according to one embodiment of the disclosure.
Figure 7:
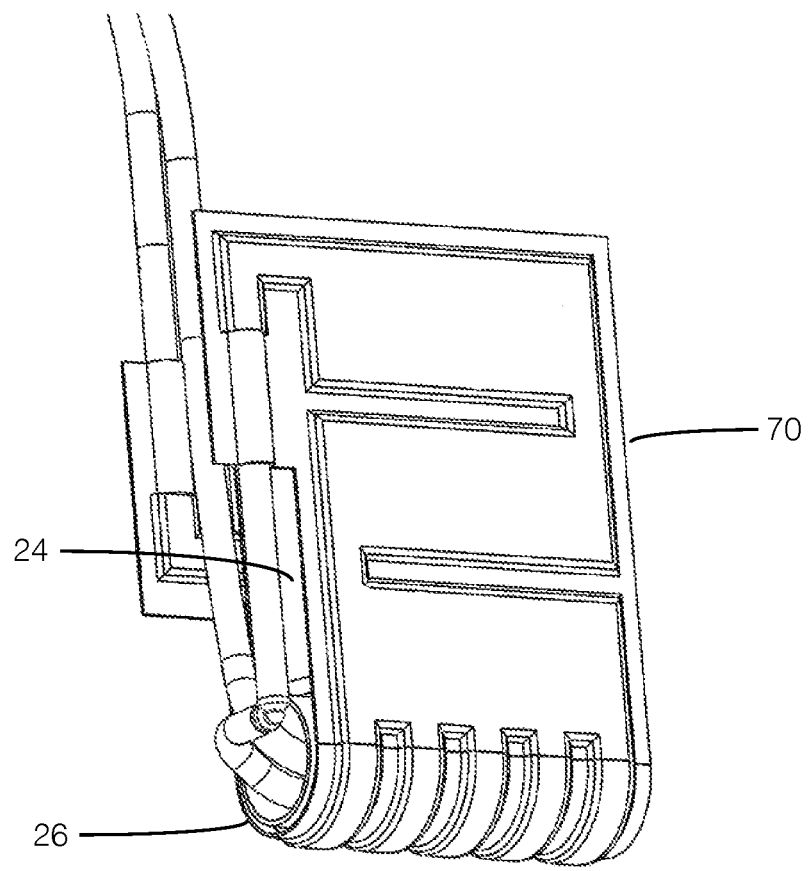
FIG. 7 shows a close-up view of a portable pump assembly of a head cooling apparatus according to one embodiment of the disclosure.
Figure 8:
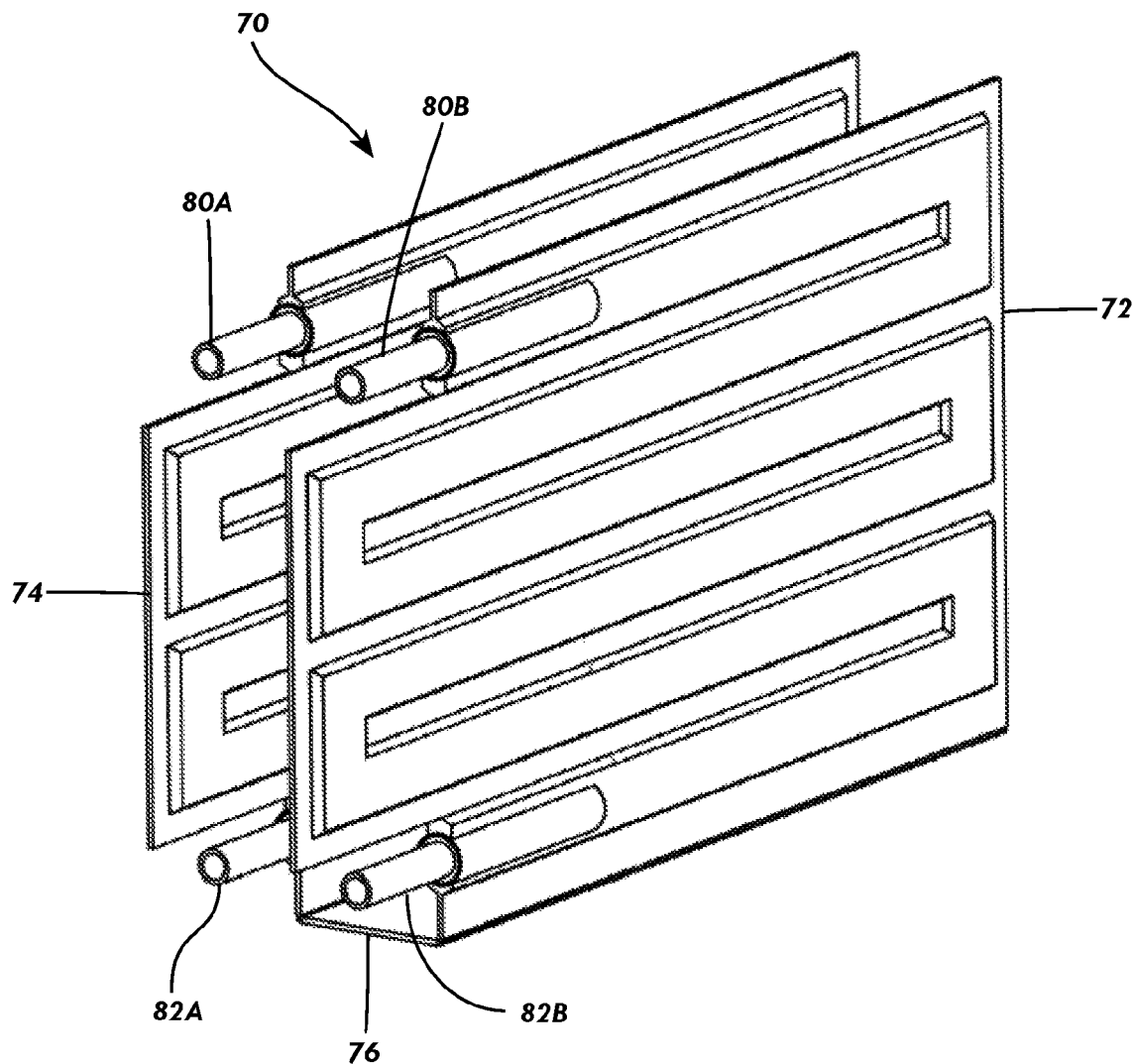
FIGS. 8-10 show a foldable heat exchanger according to one embodiment of the disclosure.

Referring to the illustration of FIG. 5, in operation, the head cooling apparatus 10 moves fluid from the portable pump assembly 12 to the headgear assembly 14 adjacent the user's head and neck to cool a head and neck of a user. The head cooling apparatus 10 is primed with a cooling fluid such as water or a non-toxic coolant such that substantially all air is removed from the head cooling apparatus 10. The replaceable cooling source 24 is inserted into the housing 20.

When the user desires to activate the head cooling apparatus, a switch 42 may be activated such that the pump 26 is powered by a power source 44 and begins pumping the fluid from the portable pump assembly 12 to the headgear assembly 14. The switch may be located on the portable pump assembly 12 or adjacent the user's head on the headgear assembly 14.

As fluid is pumped through the portable pump assembly, the fluid is cooled as it passes through the first heat exchanger 22 adjacent the replaceable cooling source 24. The cooled fluid 24 then passes through the flexible fluid transfer conduit to the headgear assembly 14 and is circulated through the second heat exchanger 30 adjacent the user's head. After circulating adjacent the user's head the fluid then exits the headgear assembly 14 through the headgear assembly outlet port and returns to the portable pump assembly 12 where the fluid is again cooled.

By priming the head cooling apparatus to remove any air and by using a pump without the use of a reservoir, the head cooling apparatus of the present disclosure is configured to advantageously provide cooling fluid to the head of the user while the user is in various orientations, such as in a lying down position. Further, the system is portable and therefore easily wearable by the user such that the user may utilize the head cooling apparatus in confined spaces. A reservoir is not required such that the head cooling apparatus is relatively lightweight and portable and such that the head cooling apparatus does not restrict movement of a user. Finally, because the replaceable cooling source is easily replaced within the housing of the portable pump assembly, when the cooling source no longer cools the fluid the cooling source may easily be swapped with a new cooling source to provide additional cooling to the user.

In one embodiment, the head cooling apparatus 10 further includes a thermostat 46 positioned adjacent the headgear assembly 14 for monitoring a temperature of the fluid. The thermostat is in electrical communication with the pump 26 such that when the temperature of a fluid rises above a desired temperature, the pump 26 is activated and the fluid is circulated through the head cooling apparatus until the temperature of the fluid is reduced below the desired temperature. When a temperature is below a desired temperature, the pump 26 is deactivated to conserve a life of the power source.

Alternatively, the head cooling apparatus 10 may include a timer in electrical communication with the pump 26 such that the pump is activated and deactivated for a desirable period of time. For example, the timer may activate the pump for approximately 1-2 minutes, followed by approximately 2-5 minutes of deactivated time of the pump. The timer may be adjustable by a user such that a period of activation and deactivation may be lengthened or shortened to account for various environmental temperatures, a temperature of a user, or other factors. The timer may optionally operate in conjunction with the thermostat to determine an amount of time to activate the pump 26. The timer and optional thermostat enable the head cooling apparatus 10 to maintain a desired temperature of a fluid within the cooling apparatus without requiring the user to manually activate the pump 26 or otherwise take action to operate the cooling apparatus 10.

In another embodiment, the portable pump assembly 12 includes additional inlet and outlet ports for securing one or more accessories to the head cooling apparatus 10. For example, additional fluid transfer conduits may be secured to the portable pump assembly 12 for cooling various other parts of the user's body, such as to a knee brace, arm brace, or other like support. Additionally, a single portable pump assembly 12 may circulate water through two or more headgear assemblies 14, wherein two or more users may wear headgear assemblies 14 which are in communication with a single portable pump assembly 12. In yet another alternative, an additional heat exchanger may be placed adjacent or around a drinking fluid bladder, such as a Camelback® style drinking pack secured to a user's back such that a fluid in the head cooling apparatus 10 is circulated through the additional heat exchanger to substantially cool a drinking fluid in the drinking fluid bladder.

While the present disclosure refers to cooling the head of a user, it is also understood that the head cooling apparatus of the present disclosure may also be used to heat various parts of a user's body by replacing the replaceable cooling source with a replaceable heat source such as hot water and/or other portable heat sources including, for example, compounds that, when mixed, produce exothermic chemical reactions and dissipate heat.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A head cooling apparatus comprising:
    a portable pump assembly including
        a replaceable cooling block,
        a first foldable heat exchanger located adjacent to the replaceable cooling source including:
            a flexible first exchanger half including a channel, an inlet port, and an outlet port;
            a center portion connected to the first exchanger half; and
            a flexible second exchanger half connected to the center portion, the second exchanger half including a channel, an inlet port, and an outlet port;
            wherein the first exchanger half and second exchanger half are foldable along the center portion such that the replaceable cooling block is sandwiched in a pocket formed between the flexible first exchanger half and flexible second exchanger half, and
        a pump in fluid communication with the first heat exchanger,
    a pack containing the portable pump assembly and worn by a user;
    a headgear assembly worn adjacent the user's head, the headgear assembly comprising a second heat exchanger positioned adjacent a user's head, a headgear assembly inlet port and a headgear assembly outlet port;
    a first flexible fluid transfer conduit connected to the outlet port of the portable pump assembly and the headgear assembly inlet port;

a second flexible fluid transfer conduit connected to the inlet port of the pump assembly and the headgear assembly outlet port;

wherein the portable pump assembly, headgear assembly, first flexible fluid transfer conduit and second fluid transfer conduit form a loop that is sealed such that no gas is present in the loop so that the portable pump assembly circulates a fluid within the loop regardless of an orientation of a user.

2. The head cooling apparatus of claim 1, wherein the second heat exchanger of the headgear assembly comprises a conformable pouch including a plurality of lobes, wherein a path is formed through the conformable pouch such that the fluid flows into the conformable pouch through the headgear assembly inlet port, through each of the lobes, and out of the headgear assembly outlet port.

3. The head cooling apparatus of claim 2, wherein the conformable pouch includes four lobes.

4. The head cooling apparatus of claim 2, wherein the conformable pouch further comprises a plurality of dimples formed therein.

5. The head cooling apparatus of claim 2, wherein the headgear assembly further comprises a head cover.

6. The head cooling apparatus of claim 5, wherein the plurality of lobes are adjustable such that one or more of the lobes may be sized to fit within various head covers.

7. The head cooling apparatus of claim 1, further comprising a thermostat in electrical communication with the pump for detecting a temperature of the fluid in either of the headgear assembly or portable pump assembly.

8. The head cooling apparatus of claim 1, wherein the pump is located adjacent to the center portion of the first foldable heat exchanger and within the pocked formed between the flexible first exchanger half and the flexible second exchanger half.

9. A head cooling apparatus comprising:
  a portable pump assembly including
    a flexible foldable heat exchanger formed into a pocket to receive a replaceable cooling block within the pocket such that the replaceable cooling block is adjacent to at least two surfaces of the flexible heat exchanger and
    a pump in fluid communication with the foldable heat exchanger and
  a headgear assembly in fluid communication with the portable pump assembly, the headgear assembly configured to be worn adjacent a user's head, the headgear assembly including a conformable pouch configured to be positioned adjacent a user's head, the conformable pouch including an inlet port and an outlet port.

10. The head cooling apparatus of claim 9 wherein the headgear assembly further comprises a head cover.

11. The head cooling apparatus of claim 9 wherein the headgear assembly includes a plurality of lobes wherein a path is formed through the conformable pouch such that a fluid flows into the conformable pouch through the headgear assembly inlet port, through each of the lobes, and out of the headgear assembly outlet port.

12. The head cooling apparatus of claim 11, wherein the conformable pouch includes four lobes.

13. The head cooling apparatus of claim 11, wherein the plurality of lobes are adjustable such that one or more of the lobes may be sized to fit within various head covers.

14. The head cooling apparatus of claim 9, wherein the conformable pouch further comprises a plurality of dimples formed therein.

15. The head cooling apparatus of claim 9, wherein the foldable heat exchanger comprises:
  a flexible first exchanger half including a channel, an inlet port, and an outlet port;
  a center portion connected to the first exchanger half; and
  a flexible second exchanger half connected to the center portion, the second exchanger half including a channel, an inlet port, and an outlet port;
  wherein the flexible first exchanger half and flexible second exchanger half are foldable along the center portion such that the replaceable cooling block is between the first exchanger half and second exchanger half.

16. The head cooling apparatus of claim 9 further comprising a thermostat in electrical communication with the pump for detecting a temperature of a fluid in either of the headgear assembly or portable pump assembly.

17. A head cooling apparatus comprising:
  a portable pump assembly including
    a foldable heat exchanger formed into a pocket to receive a replaceable cooling source, the foldable heat exchanger including:
      a flexible first exchanger half including a channel, an inlet port, and an outlet port,
      a center portion connected to the first exchanger half, and
      a flexible second exchanger half connected to the center portion, the second exchanger half including a channel, an inlet port, and an outlet port;
  a headgear assembly in fluid communication with the portable pump assembly, the headgear assembly configured to be worn adjacent a user's head, the headgear assembly including a conformable pouch configured to be positioned adjacent a user's head, the conformable pouch including an inlet port and an outlet port;
  wherein the flexible first exchanger half and flexible second exchanger half are foldable along the center portion such that a replaceable cooling source is sandwiched between the first exchanger half and second exchanger half.

* * * * *